US009823836B2

(12) United States Patent
Reynolds et al.

(10) Patent No.: US 9,823,836 B2
(45) Date of Patent: *Nov. 21, 2017

(54) MULTI-ACTION ROWS WITH INCREMENTAL GESTURES

(71) Applicant: CERNER INNOVATION, INC., Kansas City, KS (US)

(72) Inventors: Todd Jeffrey Reynolds, Kansas City, MO (US); Tyler Biethman, Overland Park, KS (US); Matt Henkes, Lee's Summit, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 707 days.

This patent is subject to a terminal disclaimer.

(21) Appl. No.: 14/341,056

(22) Filed: Jul. 25, 2014

(65) Prior Publication Data

US 2014/0337726 A1  Nov. 13, 2014

Related U.S. Application Data

(63) Continuation of application No. 13/558,972, filed on Jul. 26, 2012, now Pat. No. 8,826,128.

(51) Int. Cl.
*G06F 3/048* (2013.01)
*G06F 3/0488* (2013.01)
*G06F 19/00* (2011.01)
*G06F 3/0484* (2013.01)
*G06F 3/01* (2006.01)
*G06F 3/0481* (2013.01)

(52) U.S. Cl.
CPC ............ *G06F 3/0488* (2013.01); *G06F 3/016* (2013.01); *G06F 3/048* (2013.01); *G06F 3/0481* (2013.01); *G06F 3/04842* (2013.01); *G06F 19/3406* (2013.01)

(58) Field of Classification Search
CPC ........ G06F 3/0488; G06F 3/016; G06F 3/048; G06F 3/0481; G06F 3/04846; G06F 19/3406
USPC ......................................... 715/702
See application file for complete search history.

(56) References Cited

U.S. PATENT DOCUMENTS

| 2006/0007188 A1* | 1/2006 | Reiner | G06F 3/04883 345/179 |
| 2009/0228792 A1* | 9/2009 | van Os | G06F 3/0488 715/702 |
| 2010/0053111 A1* | 3/2010 | Karlsson | G06F 3/04883 345/174 |

(Continued)

*Primary Examiner* — David Phantana Angkool
(74) *Attorney, Agent, or Firm* — Shook, Hardy & Bacon L.L.P.

(57) ABSTRACT

Methods, computer systems, and computer storage media are provided for initiating clinical actions associated with a clinical object on a touch screen interface using incremental gestures. A clinical object is presented in an object row on the touch screen interface, and clinical actions associated with the clinical object are determined. A user gesture comprising an incremental gesture of the object row in a first direction is detected; the incremental gesture reveals an indicator associated with one of the clinical actions. The indicator is revealed after the incremental gesture has traveled a first distance. The action is initiated upon release of the incremental gesture.

20 Claims, 10 Drawing Sheets

(56) References Cited

U.S. PATENT DOCUMENTS

| | | | |
|---|---|---|---|
| 2010/0095205 A1* | 4/2010 | Kinoshita | G06F 3/0416 715/702 |
| 2011/0163968 A1* | 7/2011 | Hogan | G06F 3/04883 345/173 |
| 2011/0209104 A1* | 8/2011 | Hinckley | G06F 3/0416 715/863 |
| 2012/0030568 A1* | 2/2012 | Migos | G06F 3/0486 715/702 |
| 2012/0133600 A1* | 5/2012 | Marshall | G06F 19/321 345/173 |
| 2013/0145327 A1* | 6/2013 | Rinearson | G06F 3/017 715/863 |
| 2014/0033032 A1* | 1/2014 | Reynolds | G06F 3/048 715/702 |

* cited by examiner

FIG. 5.

MULTI-ACTION ROWS WITH INCREMENTAL GESTURES

CROSS-REFERENCE TO RELATED APPLICATION

This application having and entitled "Multi-Action Rows with Incremental Gestures" is a Continuation Application of U.S. application Ser. No. 13/558,972, filed Jul. 26, 2012, and entitled "Multi-Action Rows with Incremental Gestures." The entirety of the aforementioned application is incorporated by reference herein.

BACKGROUND

Many software applications in existence today allow for multiple actions to be taken against a single piece of data. This presents a design challenge for user interfaces especially touch screen interfaces. When multiple actions are presented all at once on the user interface, the actions can clutter the user's view, cause confusion, obscure other information on the user interface, and decrease overall usability. One way of presenting actions requires the user to perform multiple touches or selections and navigate to different user interfaces or menu/sub-menu systems to view the full range of actions.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief, and at a high level, methods, systems, and computer storage media provide for initiating one or more clinical actions associated with a clinical object on a touch screen interface using incremental gestures. A clinical object is presented in an object row on the touch screen interface. Actions associated with the clinical object are hidden from view. A user reveals the presence of one or more of the clinical actions by performing an incremental gesture such as a pull of the object row. A pull of a first distance and first direction reveals a first clinical action with respect to the clinical object, a pull of a second distance and second direction reveals a second clinical action, and so on. A clinical action is initiated after the user pulls the object row to fully reveal a label associated with the clinical action and then releases the pull. The result is a streamlined user interface that still offers access to a wide range of clinical actions with respect to a clinical object.

BRIEF DESCRIPTION OF THE DRAWINGS

Embodiments are described in detail below with reference to the attached drawings figures, wherein:

FIG. 5 depicts the exemplary touch screen interface illustrating the presentation of sub-clinical actions in response to the initiation of the first clinical action;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer storage media for initiating one or more clinical actions associated with a clinical object on a touch screen interface using incremental gestures. A clinical object is presented in an object row on the touch screen interface. Actions associated with the clinical object are hidden from view. A user reveals the presence of one or more of the clinical actions by performing an incremental gesture such as a pull of the object row. A pull of a first distance and first direction reveals a first clinical action with respect to the clinical object, a pull of a second distance and second direction reveals a second clinical action, and so on. A clinical action is initiated after the user pulls the object row to fully reveal a label associated with the clinical action and then releases the pull. The result is a streamlined user interface that still offers access to a wide range of clinical actions with respect to a clinical object.

Figure 1:
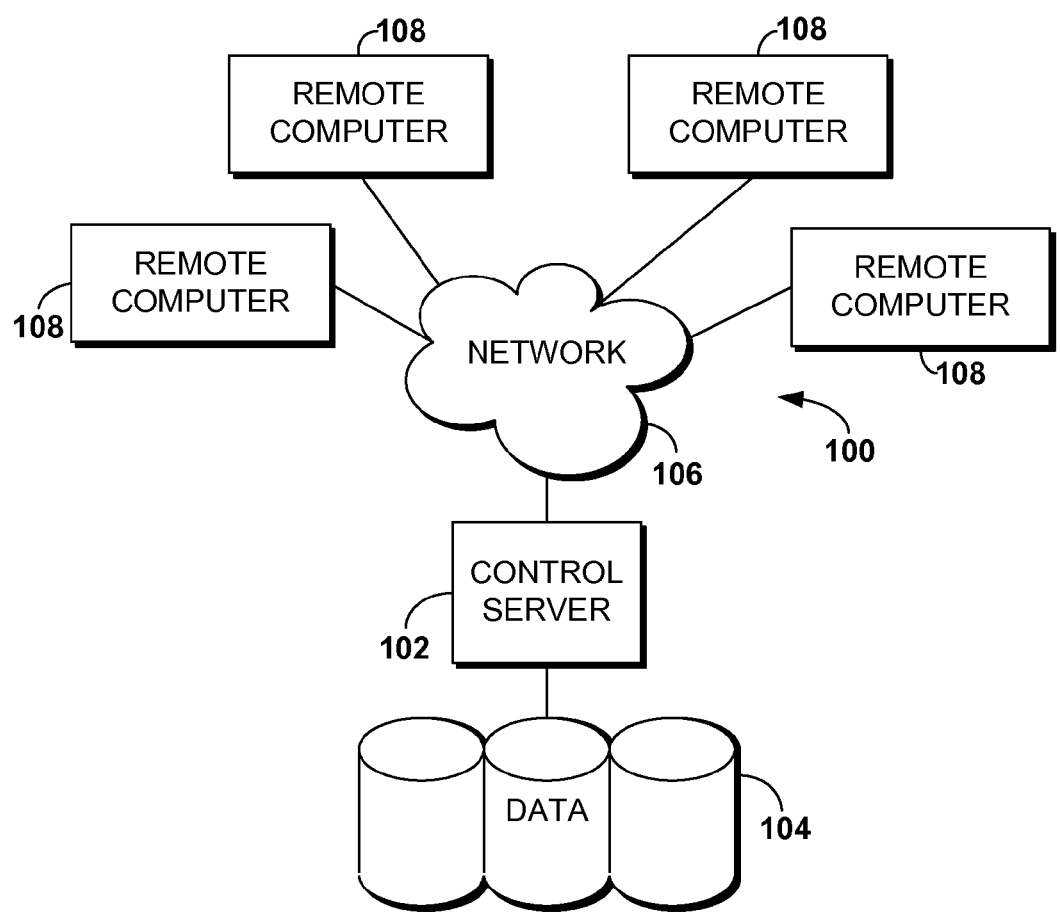
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
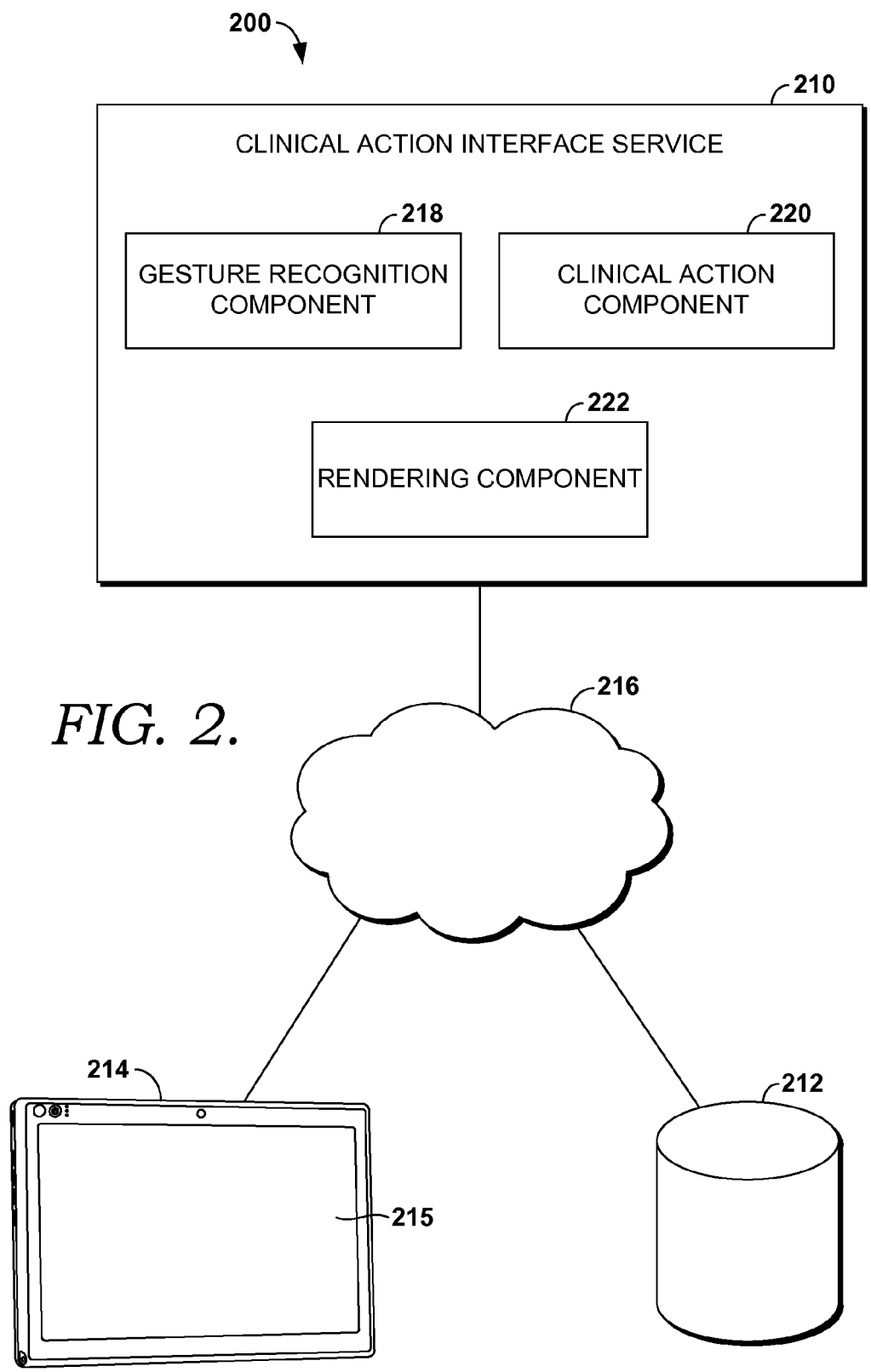
FIG. 2 is a block diagram of an exemplary system for initiating clinical actions using incremental gestures suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a clinical action interface service 210, a data store 212, and an end-user computing device 214 with a display screen 215 all in communication with one another via a network 216. The network 216 may include, without limitation, one or more local area networks (LANs) and/or wide area networks (WANs). Such networking environments are commonplace in offices, enterprise-wide computer networks, intranets and the Internet. Accordingly, the network 216 is not further described herein.

In some embodiments, one or more of the illustrated components/modules may be implemented as stand-alone applications. In other embodiments, one or more of the illustrated components/modules may be integrated directly into the operating system of the clinical action interface service 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the clinical action interface service 210 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 212 is configured to store information for use by, for example, the clinical action interface service 210. The information stored in association with the data store 212 is configured to be searchable for one or more items of information stored in association therewith. The information stored in association with the data store 212 may comprise general information used by the clinical action interface service 210.

For example, the data store 212 may store electronic medical records (EMRs) of patients associated with one or more healthcare facilities. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

The content and volume of such information in the data store 212 are not intended to limit the scope of embodiments of the present invention in any way. Further, though illustrated as a single, independent component, the data store 212 may, in fact, be a plurality of storage devices, for instance, a database cluster, portions of which may reside on the clinical action interface service 210, the end-user computing device 214, and/or any combination thereof.

As shown, the end-user computing device 214 includes a display screen 215. The display screen 215 is configured to display information to the user of the end-user computing device 214, for instance, information relevant to communications initiated by and/or received by the end-user computing device 214, ordering information, problem lists, and/or the like. Embodiments are not intended to be limited to visual display but rather may also include audio presentation, combined audio/visual presentation, and the like. The end-user computing device 214 may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions.

In one aspect, the display screen 215 is a touch screen interface. The touch screen interface allows for direct interaction with the screen 215 without any hardware between the user and the content on the screen and is commonly seen with smart phones and tablet PCs. The touch screen interface may use a variety of technologies to sense the touch of a user. Such technologies include resistive, surface acoustic wave, capacitive, infrared, optical imaging, dispersive signal technology, acoustic pulse recognition, and the like.

Components of the clinical action interface service 210 may include a processing unit, internal system memory, and a suitable system bus for coupling various system components, including one or more data stores for storing information (e.g., files and metadata associated therewith). The clinical action interface service 210 typically includes, or has access to, a variety of computer-readable media.

The computing system environment 200 is merely exemplary. While the clinical action interface service 210 is illustrated as a single unit, it will be appreciated that the clinical action interface service 210 is scalable. For example, the clinical action interface service 210 may in actuality include a plurality of computing devices in communication with one another. Moreover, the data store 212, or portions thereof, may be included within, for instance, the clinical action interface service 210 as a computer-storage medium. The single unit depictions are meant for clarity, not to limit the scope of embodiments in any form.

As shown in FIG. 2, the clinical action interface service 210 comprises a gesture recognition component 218, a clinical action component 220, and a rendering component 222. In some embodiments, one or more of the components 218, 220, and 222 may be implemented as stand-alone applications. In other embodiments, one or more of the components 218, 220, and 222 may be integrated directly into the operating system of a computing device such as the remote computer 108 of FIG. 1. It will be understood that the components 218, 220, and 222 illustrated in FIG. 2 are exemplary in nature and in number and should not be construed as limiting. Any number of components may be employed to achieve the desired functionality within the scope of embodiments hereof.

The gesture recognition component 218 is configured to recognize a variety of user gestures with respect to a touch screen interface such as the touch screen interface 215. User gestures recognized by the gesture recognition component 218 include taps, double-taps, holds, pinches, swipes, drags, and flicks. These actions are often used to initiate a single action with respect to an object or to initiate the display of a menu where further user gestures are required to initiate an action.

In one aspect, the gesture recognition component 218 is configured to recognize an incremental gesture of an object row on the touch screen interface. The incremental gesture may comprise a pull of the object row or a push of the object row. For instance, an incremental gesture may include a pull of the object row in a right-to-left direction, a left-to-right direction, or a top-to-bottom direction. A push incremental gesture may comprise a push of the object row in a bottom-to-top direction. Pulls and/or pushes in diagonal directions are also contemplated.

The object row presents an object; the object is associated with a number of actions. However, to avoid clutter, the actions are not presented on the object row in association with the object. To reveal one of the actions, the user may pull or push the edge of the object row which, in turn, sequentially reveals an indicator associated with the action on the touch screen interface. The indicator may include a textual label identifying the action. Other examples of indicators include icons or audio snippets identifying the action. As the user continues to pull/push the object row, a second indicator associated with a second clinical action is sequentially revealed. Once the user reaches the indicator associated with the desired action, as demonstrated by the indicator associated with the desired action being fully revealed, the user releases the incremental gesture of the object row to initiate the desired action. Each action is associated with a gesture of a certain distance and a certain direction.

The gesture recognition component 218 is also configured to recognize whether the user successfully completes an incremental gesture. A successful gesture comprises a pull/push of a predetermined distance in a predetermined direction, and a release of that pull. A small margin of error with respect to the predetermined distance may be built in to increase usability of the interface. One way of training a user to complete a successful incremental gesture is to provide a tactile indication indicating that the user has reached the predetermined distance. The tactile indication may include a vibration or a slight, temporary sticking of the pull. Auditory indications may be used as well such as beeping, pinging, and the like. Visual indications such as flashing or a color-change may also be used to indicate that the user has reached the predetermined distance.

To further increase the probability of successful incremental gestures, the gesture recognition component 218 may be configured to provide tutorials to users regarding how to successfully use incremental gestures. The tutorial may be presented the first time the user is exposed to incremental gestures. As well, tutorials may be presented upon determining that the user is having difficulty with the incremental gesture (i.e., a low percentage of successful incremental gestures).

Different actions may be associated with different sides of the object row. For simplicity purposes, a left side and a right side of the object row will be discussed but the discussion is equally applicable to a bottom and a top of the object row. The user can invoke a first set of actions by pulling the object row from the right and invoke a second set of actions by pulling the object row from the left. Using incremental pulls, anywhere from 8 to 10 actions may be invoked for a single object while maintaining a streamlined view of the touch screen interface.

Further, actions may grouped into logical groupings, and one group may be located on the right side of the object row and a second group may be located on the left side of the object row. For instance, actions may be grouped into positive actions and negative actions. Using a medication order as an example, the medication is considered the object, and the actions associated with the object include, for example, refill, continue, modify, copy, discontinue, complete, cancel, void, and delete. Positive actions may include refill, continue, modify, complete, and copy, while negative actions may include discontinue, cancel, void, and delete. The positive actions may be invoked, for example, by interacting with the right side of the object row, and the negative actions may be invoked by interacting with the left side of the object row.

The clinical action component 220 is configured to determine actions associated with an object. Common actions may be shared between different objects. For example, common actions associated with different medications include refill, continue, cancel, and the like. Actions may also vary depending on the identity of the object. For instance, one medication may have a different route of administration as compared to another medication. Or when the object is a problem such as allergies, actions may include "no known drug allergies," "known drug allergies" "unable to obtain allergy information," and the like.

Actions associated with an object may dynamically change depending upon actions that have been initiated for the object. The object may initially be associated with a group of actions. In response to a user invoking a first action, the clinical action component 220 may modify the remaining actions for the object. One modification may include removing the selected action from the list of available actions. Another modification may include making the only available action for the object an undo action, selection of which undoes the initially selected action. By way of illustrative example, an action invoked for a medication may be a refill action. After this action is invoked, the clinical action component 220 may eliminate all other actions associated with the medication except an undo action that undoes the refill action. Another modification may include adding an undo action to the group of actions after a first action has been initiated. Yet another modification may include making any subsequent action an undo action of the first action regardless of the nature of the action. Any and all such variations are within the scope of embodiments of the invention.

Further, the clinical action component 220 is configured to determine sub-actions associated with an invoked action. Using baseball as an example, actions associated with an object such as the player at bat include, for example, hit, error, and out. If the hit action is invoked, sub-actions determined for the hit action include single, double, triple, and home run. These sub-actions may be presented to the user using incremental gestures, or, alternatively, the sub-actions may be presented in association with the object on the object row. In the first case, the user initiates a sub-action by performing an incremental gesture having a first distance and a first direction, while in the second case, the user initiates a sub-action by performing a user gesture such as a tap.

The clinical action component 220 is also configured to initiate a clinical action upon receiving an indication that an incremental gesture has been successfully completed with respect to the clinical action. The indication may be received from the gesture recognition component 218. Documentation that the clinical action has been initiated may be stored in association with the data store 212.

The rendering component 222 is configured to render the object rows and the actions on the touch screen interface. The rendering component may render multiple object rows on the touch screen interface, each object row having a different object and possibly a different set of actions associated with the object. The rendering component 222 is also configured to render visual indicators in association with the object row to indicate, for example, the successful initiation of an action or the unsuccessful initiation of an action. A successful or unsuccessful initiation of an action may be indicated by a color-coded bar at the end of the object row; the bar is located on the side of the object row from which the incremental gesture was initiated. A successful initiation of an action may be indicated, for example, by a green-colored bar at the end of the object row, while an unsuccessful initiation may be indicated by, for example, a red-colored bar at the end of the object row. In an alternative aspect, successful initiation of a positive action may be indicated by a colored bar of one color, while successful initiation of a negative action may be indicated by a different colored bar. Any and all such aspects are within the scope of embodiments of the invention.

The rendering component 222 is also configured to present a textual label indentifying the action on the object row after the action has been successfully initiated. This enables the user to quickly see what action is currently in effect for the object. If an action is associated with one or more sub-actions, the rendering component 222 may present the sub-actions on the object row after the action has been initiated.

Figure 3:
FIG. 3 depicts an exemplary touch screen interface illustrating a medication order form according to an embodiment of the present invention.

Turning now to FIG. 3, FIG. 3 depicts an exemplary touch screen interface 300. The touch screen interface 300 may be presented on a smart phone, a tablet PC, and the like. The touch screen interface 300 includes a header 310 that provides a general description of the objects that are presented in the object rows. The touch screen interface 300 further includes object rows 312. In this case, the objects in the object rows 312 include medications having names and other identifying information (dosage, route of administration, etc.). The touch screen interface 300 includes, for example, an object row 314 that consists of the object "aspirin." The aspirin object row 314 has a list of sub-actions 316 that are currently not available because no action has been initiated for the aspirin object row 314. This may be shown on the touch screen interface 300 by "graying out" the sub-actions 316. In one aspect, no sub-actions are presented (grayed out or not) until an action has been initiated.

The touch screen interface 300 further includes an indicator 318 (e.g, a colorless or grayed-out bar) that indicates that the right side of the aspirin object row 314 can be used to initiate actions for the aspirin object. Although not shown, an indicator may also be located on the opposite side of the aspirin object row 314 if further actions can be initiated from that side. Once an action has been initiated, the indicator 318 may be colored to indicate that the action was successfully initiated. The touch screen interface 300 may also include an arrow 320. Selection of the arrow 320 provides more detailed information about the aspirin object.

Figure 4:
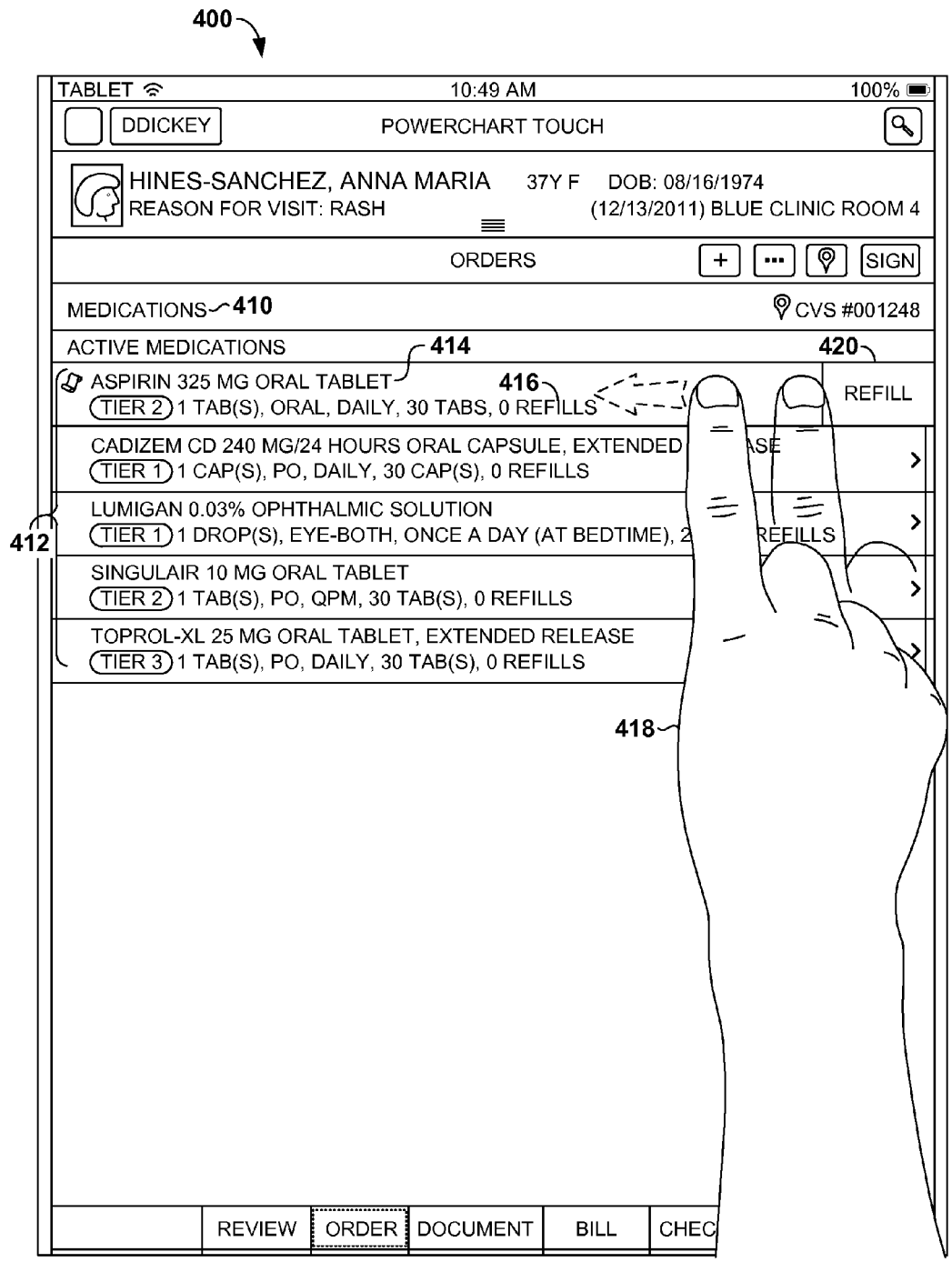
FIG. 4 depicts the exemplary touch screen interface illustrating a first incremental pull revealing a first clinical action associated with a medication order according to an embodiment of the present invention.

FIG. 4 depicts the same touch screen interface as FIG. 3 (now labeled as touch screen interface 400). Similar to FIG. 3, the touch screen interface 400 includes header 410, object rows 412, aspirin object row 414, and unavailable sub-actions 416. FIG. 4 illustrates an incremental gesture 418 associated with the aspirin object row 414. The incremental gesture 418 begins at the right-hand side of the aspirin object row 414 and moves to the left. In this case, the incremental gesture 418 has revealed action label 420 associated with a refill action. The action label 420 is not revealed until the incremental gesture 418 has traveled a first distance. Thus, the action label 420, and its associated action, is associated with an incremental gesture of a first distance and a first direction (in this case, the direction is to the left). The incremental gesture 418 may be associated with a tactile, auditory, or visual indication letting the user know that if the user chose to release the incremental gesture 418 at the indicated point, the revealed action would be initiated.

Figure 5:
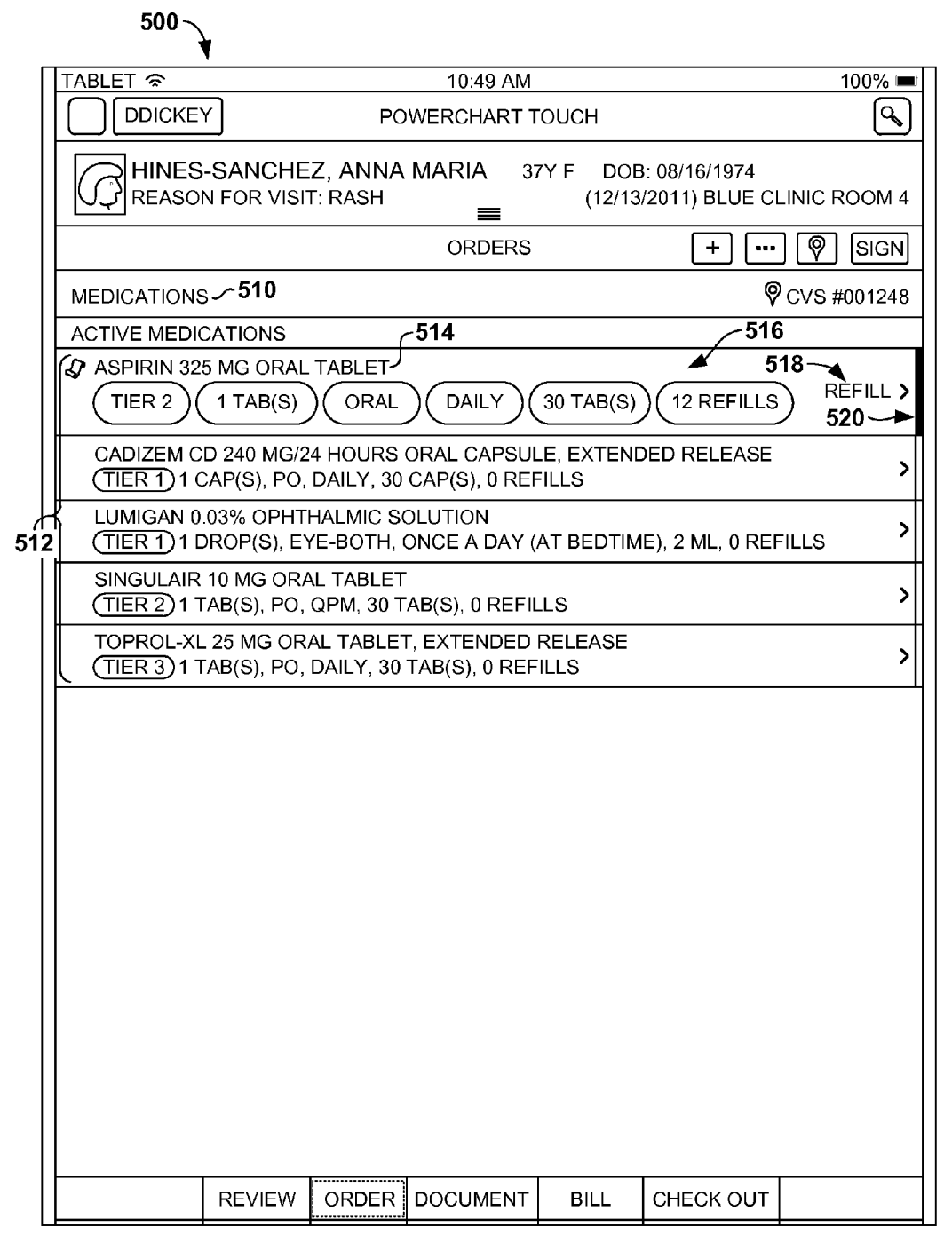

FIG. 5 depicts the same touch screen interface as FIG. 4 (now labeled as touch screen interface 500) at a slightly later point in time. Like FIG. 4, the touch screen interface 500 includes header 510, object rows 512, and aspirin object row 514. In the case of the touch screen interface 500, however, the refill action of FIG. 4 has been initiated. This is shown by label 518 (Refill) and visual indicator 520. The visual indicator 520 is similar to the indicator 318 in FIG. 3 but is now color-coded instead of clear or grayed-out. The visual indicator 520 may be any color such as, for example, green. The touch screen interface 500 further includes sub-actions 516 represented by actionable buttons. A user selection (e.g., a user tap) of one of the sub-actions 516 initiates the selected sub-action. In one aspect, the sub-actions may be hidden and incremental gestures can be used to reveal and initiate the sub-actions.

Figure 6:
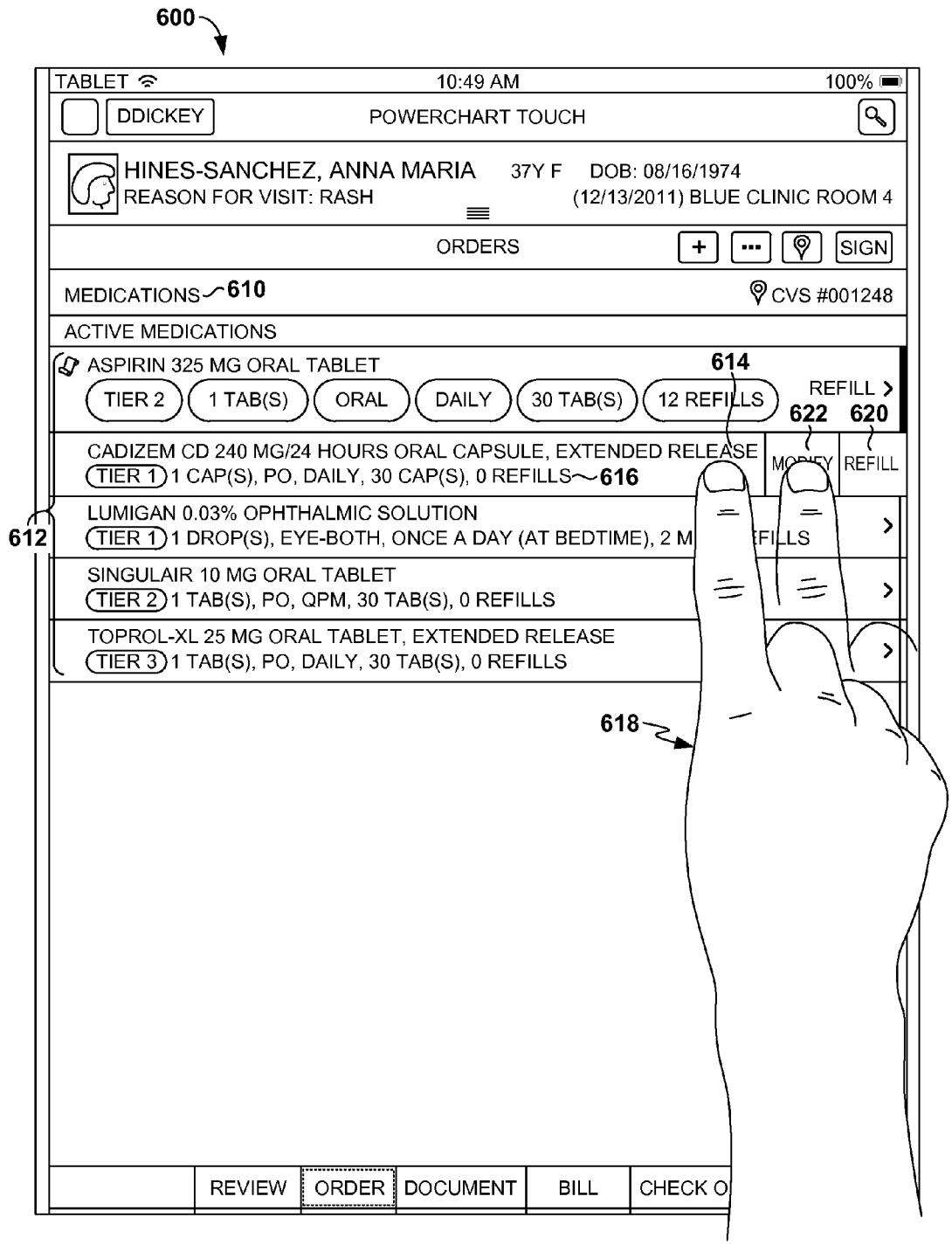
FIG. 6 depicts the exemplary touch screen interface illustrating a second incremental pull revealing a second clinical action associated with a medication order according to an embodiment of the present invention.

Turning to FIG. 6, FIG. 6 depicts the same touch screen interface as FIG. 5 (now labeled as touch screen interface 600) at a still later point in time. The touch screen interface 600 includes header 610, object rows 612, and a Cadizem object row 614. An incremental gesture 618 is shown. The incremental gesture 618 has revealed a first action label 620 associated with a refill action and a second action label 622 associated with a modify action. Like above, the second action label 622 is revealed after the incremental gesture 618 has traveled a predetermined distance. If the user were to continue the incremental gesture 618, additional labels associated with additional actions may be revealed. The actions 620, 622 are differentiated based on a distance of the incremental gesture 618. The actions 620, 622 may also be associated with different colors, different tactile indications, different auditory indications, and the like. The touch screen interface further includes unavailable sub-actions 616; the sub-actions 616 are currently not actionable because an action has not been initiated.

Figure 7:
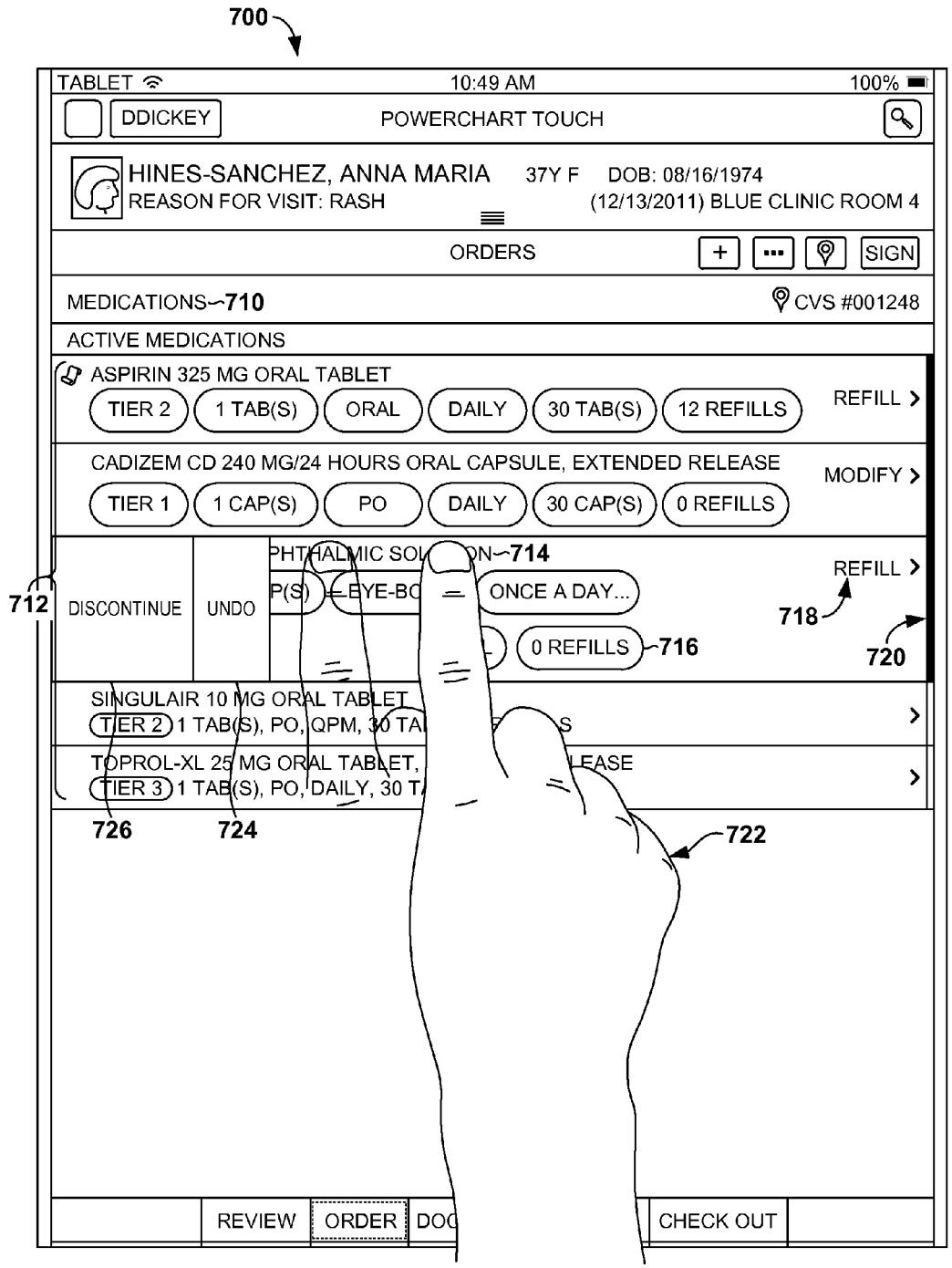
FIG. 7 depicts the exemplary touch screen interface illustrating an incremental pull revealing an undo action according to an embodiment of the present invention.

FIG. 7 depicts a touch screen interface 700 that is the same as the touch screen interface 600 but is at a later point in time. The touch screen interface 700 includes a header 710, object rows 712, and a Lumigan object row 714. Visual indicators 718 and 720 indicate that a refill action has previously been initiated for the Lumigan object row 714. As well, sub-actions 716 are currently available. The touch screen interface 700 further demonstrates an undo action label 724 associated with an undo action. The undo action label 724 has been pulled onto the touch screen interface 700 by an incremental gesture 722 of a first distance. In this case, the incremental gesture 722 is to the right and the undo action label 724 is on the left-hand side of the object row 714. The touch screen interface 700 also demonstrates a discontinue action label 726 associated with a discontinue action on the left-hand side of the object row 714. The discontinue action label 726 has been pulled onto the touch screen interface 700 by having the incremental gesture 722 travel a second distance.

Figure 8:
FIG. 8 depicts the exemplary touch screen interface illustrating the presentation of a sub-clinical action related to the undo action according to an embodiment of the present invention.

FIG. 8 depicts a touch screen interface 800 that illustrates the initiation of the discontinue action of FIG. 7. The touch screen interface 800 includes a header 810, object rows 812, and a Lumigan object row 814. The Lumigan object row 814 includes a visual indicator 822 indicating that an action has been initiated from the left-hand side of the object row 814. Further, the Lumigan object row 814 also includes a visual indicator 818 indicating that the discontinue action has been initiated. A "reason" sub-action 816 is also presented in response to the initiation of the discontinue action. A user may select the "reason" sub-action 816 and input a reason why the medication was discontinued. The visual indicators and sub-actions associated with the previous refill action for the Lumigan object row 814 are no longer presented.

In one aspect of the invention, a single gesture can be used to initiate an action for all the object rows at once. For example, the object rows may each be associated with a medication, and a clinician wishes to initiate a refill action for all of the medications. Such an action could be initiated by, for example, performing an incremental gesture on the header associated with the touch screen interface (e.g., the header 810 of FIG. 8). Other ways of initiating the action may include doing a multi-finger diagonal sweep across all the object rows.

Figure 9:
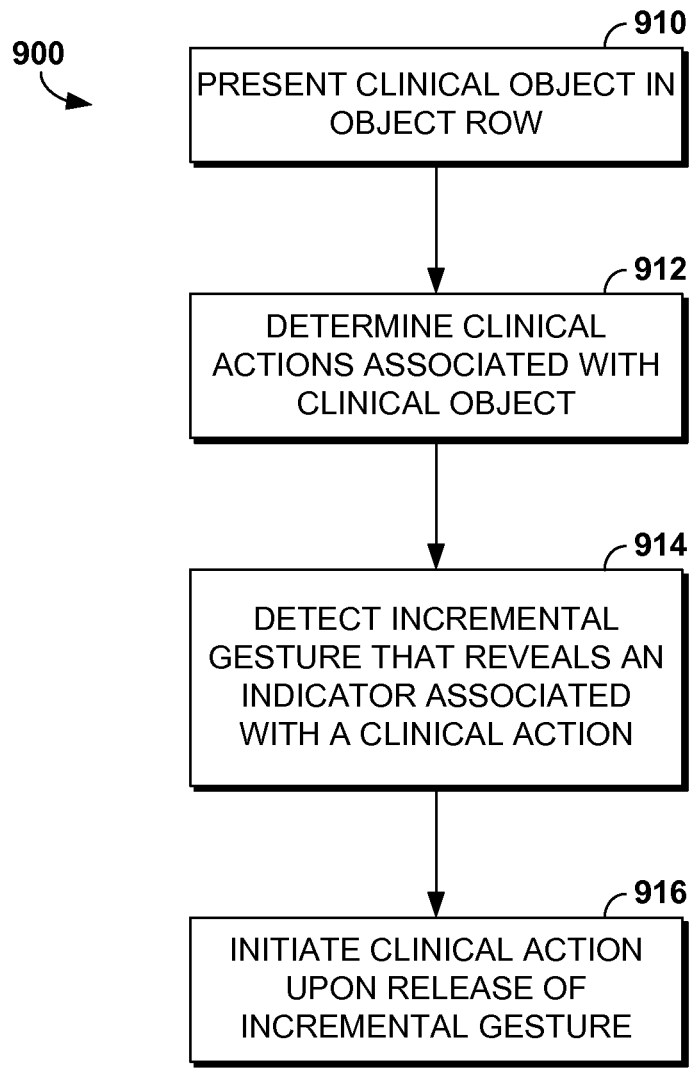
FIGS. 9-10 are flow diagrams that illustrate exemplary methods of initiating one or more clinical actions associated with a clinical object on a touch screen interface using incremental gestures according to an embodiment of the present invention.

Turning now to FIG. 9, a flow diagram is depicted of an exemplary method 900 of initiating one or more clinical actions associated with a clinical object on a touch screen interface using incremental gestures. At a step 910, a clinical object is presented in a clinical object row on a touch screen interface by a rendering component such as the rendering component 222 of FIG. 2. Clinical objects may include, for example, orders, medications, labs, procedures, problems, diagnoses, and the like. At a step 912, clinical actions associated with the clinical object are determined by, for example, a clinical action component such as the clinical action component 220 of FIG. 2. Clinical actions associated with, for example, a medication order may include refill, continue, modify, copy, discontinue, complete, cancel, undo, void, and delete.

At a step 914, a user gesture related to the object row is detected by, for example, a gesture recognition component such as the gesture recognition component 218 of FIG. 2. The user gesture may comprise an incremental gesture of the object row in a first direction to sequentially reveal a first indicator associated with a first clinical action of the determined clinical actions. The first indicator may include a textual label, an icon, an audio snippet, and the like identifying the first clinical action. The first indicator is revealed after the first incremental gesture has traveled a first distance. The first direction may include a left-to-right direction, a right-to-left direction, a top-to-bottom direction, or a bottom-to-top direction. At a step 916, the clinical action is initiated subsequent to the user releasing the incremental gesture.

The method 900 may further comprise detecting additional incremental gestures with respect to the clinical object. The additional incremental gestures are associated with different clinical actions than the first clinical action and comprise different distances than the first incremental gesture. Further, the additional incremental gestures may be in the same direction as the first incremental gesture, or they may be in the opposite direction as the first incremental gesture. Upon invocation of a different clinical action, the first clinical action may be undone or revoked. In one aspect, the second clinical action is an undo action. In another aspect, the second clinical action is an action other than an undo action.

Figure 10:
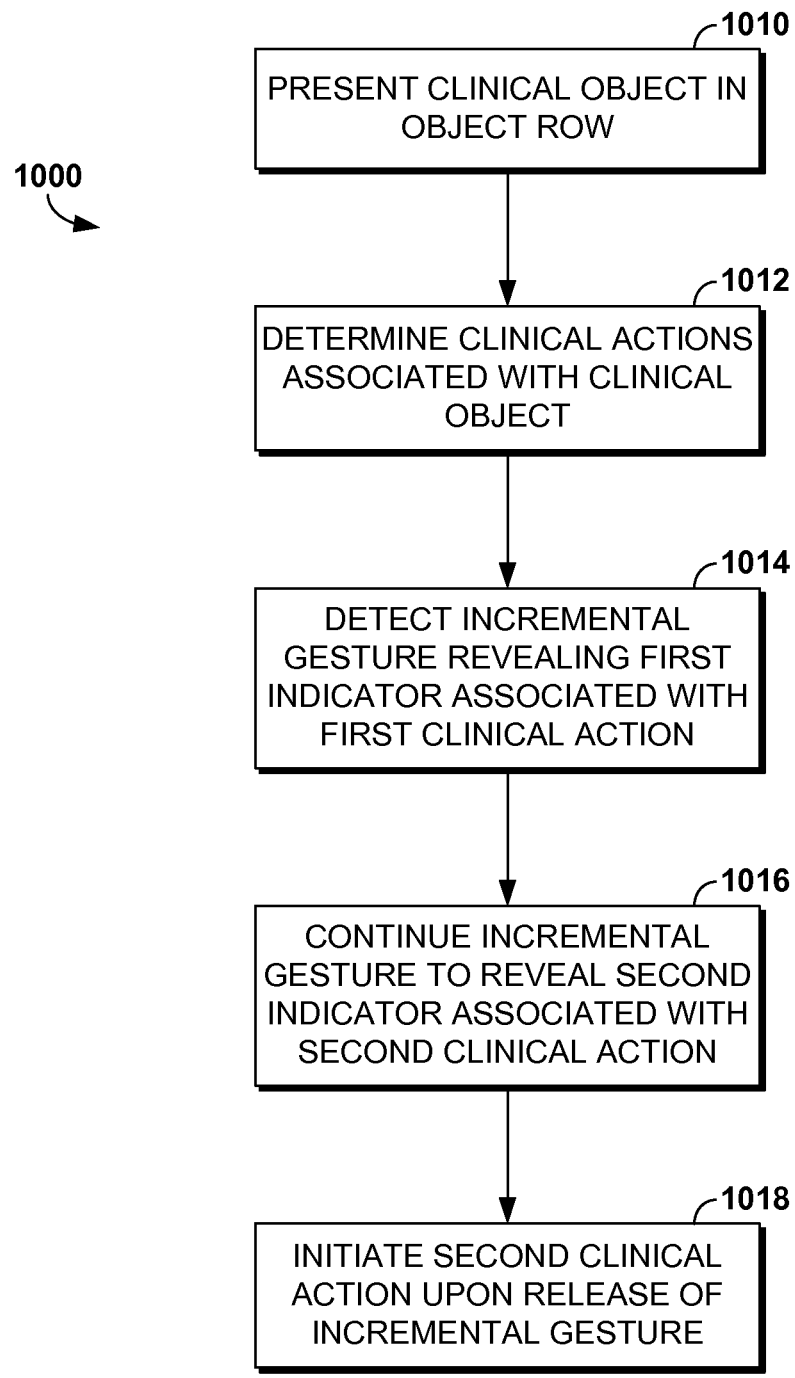

FIG. 10 depicts another flow diagram of an exemplary method 1000 of initiating one or more clinical actions associated with a clinical object on a touch screen interface using incremental gestures. At a step 1010, a clinical object in an object row is presented on a touch screen interface, and, at a step 1012, clinical actions associated with the clinical object are determined. The clinical actions are dependent on the identity and characteristics of the clinical object.

At a step 1014, an incremental gesture of the object row is detected. The incremental gesture is in a first direction and has a first distance and reveals a first indicator associated with a first clinical action. At a step 1016, the incremental gesture continues in the first direction and reveals a second indicator associated with a second clinical action. The second clinical action is associated with a second distance traveled by the incremental gesture. At a step 1018, the second clinical action is initiated upon release of the incremental gesture.

Upon initiation of the second clinical action, a set of sub-actions corresponding to the second clinical action may be determined. The sub-actions may be presented on the object row, or, alternatively, the sub-actions may be revealed through the use of incremental gestures. By way of illustrative example, an action may comprise a refill action, and the refill action may be associated with a set of sub-actions comprising different dosage amounts and routes of administration. Upon initiation of the refill action, the sub-actions may be presented on the object row, or the sub-actions may be revealed by using incremental gestures. In this case, the initial set of actions associated with the object is replaced with the sub-actions associated with the selected action.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computerized method, carried out by a server running on one or more processors, of initiating one or more clinical actions associated with a clinical object on a touch screen interface using incremental gestures, the method comprising:

determining a first set of clinical actions associated with the clinical object, wherein the first set of clinical actions is determined based on characteristics of the clinical object;

presenting the clinical object in an object row on the touch screen interface;

detecting, using the one or more processors, a first incremental gesture related to the object row on the touch screen interface, the first incremental gesture comprising a push or a pull of the object row in a first direction and a first distance to reveal a first indicator associated with a first clinical action of the first set of clinical actions;

initiating the first clinical action of the first set of clinical actions upon release of the first incremental gesture; and subsequent to the first clinical action being initiated, determining a second set of clinical actions associated with the clinical object, wherein an indicator associated with at least one clinical action of the second set of clinical actions is revealed upon detecting a second incremental gesture of the object row on the touch screen interface, the second incremental gesture comprising a push or pull of the object row in a second direction and a second distance.

2. The computerized method of claim 1, wherein the first direction is the same as the second direction.

3. The computerized method of claim 1, wherein the first direction is different from the second direction.

4. The computerized method of claim 1, wherein the first distance is the same as the second distance.

5. The computerized method of claim 1, wherein the first distance is different from the second distance.

6. The computerized method of claim 1, wherein the first set of clinical actions is replaced with the second set of clinical actions.

7. The computerized method of claim 1, wherein the second set of clinical actions comprises a subset of the first set of clinical actions.

8. The computerized method of claim 7, wherein the second set of clinical actions further comprises one or more additional actions.

9. The computerized method of claim 1, wherein the second set of clinical actions comprises sub-actions that correspond to the first set of clinical actions.

10. The computerized method of claim 1, wherein the second set of clinical actions comprises an undo action.

11. A computerized system for detecting incremental gestures related to a clinical object and initiating clinical actions based on the incremental gestures, the system comprising:

a clinical action interface service comprising one or more processors; and one or more computer storage media storing computer-useable instructions that, when used by the one or more processors, cause the one or more processors to:

determine a first set of clinical actions associated with the clinical object, wherein the first set of clinical actions is determined based on an identity of the clinical object;

present the clinical object and the first set of clinical actions on an object row of a touch screen interface, wherein the clinical object is presented such that it is visible to a user, and wherein the first set of clinical actions is initially hidden from the user's view;

detect a first incremental gesture related to the object row, the first incremental gesture comprising a push or pull of the object row in a first direction and a first distance to reveal a first indicator associated with at least one of the first set of clinical actions;

initiate the at least one of the first set of clinical action upon release of the first incremental gesture;

determine a second set of clinical actions associated with the clinical object;

continue to present the clinical object on the object row of the touch screen interface and replace the first set of clinical actions with the second set of clinical actions, wherein the second set of clinical actions is initially hidden from the user's view;

detect a second incremental gesture related to the object row, the second incremental gesture comprising a push or pull of the object row in a second direction and a second distance to reveal a second indicator associated with at least one of the second set of clinical actions; and initiate the at least one of the second set of clinical actions upon release of the second incremental gesture.

12. The computerized system of claim 11, wherein the first direction of the first incremental gesture comprises a push or a pull of the object row in a right direction, a left direction, a down direction, or an up direction.

13. The computerized system of claim 11, wherein the second direction of the second incremental gesture comprises a push or a pull of the object row in a right direction, a left direction, a down direction, or an up direction.

14. The computerized system of claim 11, wherein the first and second incremental gestures are each associated with a tactile sensation indicating that the respective first and second indicators have been revealed.

15. The computerized system of claim 14, wherein the tactile sensation comprises a temporary sticking point.

16. One or more non-transitory computer storage media having embodied thereon computer-executable instructions that, when executed by a server, perform a method of initiating clinical actions related to a clinical object upon detection of an incremental gesture at a touch screen interface, the method comprising:

presenting the clinical object in an object row on the touch screen interface;

determining a first set of clinical actions associated with the clinical object, wherein the first set of clinical actions comprises actions available with respect to the clinical object;

detecting a first incremental gesture on the touch screen interface comprising a pull or push of the object row in a first direction and a first distance to reveal a first indicator associated with a first clinical action of the first set of clinical actions;

initiating the first clinical action upon user release of the incremental gesture;

determining a second set of clinical actions associated with the clinical object;

detecting a second incremental gesture on the touch screen interface comprising a pull or push of the object row in a second direction and a second distance to reveal a second indicator associated with a second clinical action of the second set of clinical actions; and initiating the second clinical action of the second set of clinical actions upon user release of the second incremental gesture.

17. The media of claim 16, wherein a first color indicator is presented on the object row subsequent to the initiation of the first clinical action, the first color indicator indicating that the initiation of the first clinical action was successful.

18. The media of claim 17, wherein a second color indicator is presented on the object row subsequent to the initiation of the second clinical action, the second color indicator indicating that the initiation of the second clinical action was successful.

19. The media of claim 16, wherein the first set of clinical actions comprises one or more of the following: refill, continue, modify, copy, discontinue, complete, cancel, void, and delete.

20. The media of claim 16, wherein the second set of clinical actions comprises an undo action.

\* \* \* \* \*